(12) United States Patent
Wachtel

(10) Patent No.: US 7,694,676 B2
(45) Date of Patent: Apr. 13, 2010

(54) DRY POWDER INHALER

(75) Inventor: Herbert Wachtel, Ingelheim (DE)

(73) Assignee: Boehringer Ingelheim GmbH, Ingelheim am Rhein (DE)

( * ) Notice: Subject to any disclaimer, the term of this patent is extended or adjusted under 35 U.S.C. 154(b) by 689 days.

(21) Appl. No.: 11/113,091

(22) Filed: Apr. 22, 2005

(65) Prior Publication Data

US 2006/0237016 A1    Oct. 26, 2006

(51) Int. Cl.
    *A61M 15/00*     (2006.01)
    *A61M 16/00*     (2006.01)

(52) U.S. Cl. .............................. 128/203.21; 128/203.15

(58) Field of Classification Search ............ 128/200.24, 128/203.15, 203.14, 203.19, 203.21; 222/80, 222/153.1, 189.06, 472; 206/528, 532, 531, 206/530, 534

See application file for complete search history.

(56) References Cited

U.S. PATENT DOCUMENTS

| | | | | |
|---|---|---|---|---|
| 3,724,459 A | * | 4/1973 | Congro ................. | 128/203.22 |
| 4,860,740 A | * | 8/1989 | Kirk et al. ............. | 128/203.15 |
| 5,575,280 A | * | 11/1996 | Gupte et al. ........... | 128/203.15 |
| 5,685,294 A | * | 11/1997 | Gupte et al. ........... | 128/203.15 |
| 5,685,894 A | | 11/1997 | Bowerman et al. | |
| 5,787,881 A | * | 8/1998 | Chawla ................. | 128/203.15 |
| 5,947,118 A | * | 9/1999 | Hochrainer et al. .... | 128/203.15 |
| 6,055,980 A | * | 5/2000 | Mecikalski et al. .... | 128/203.15 |
| 6,182,655 B1 | * | 2/2001 | Keller et al. ........... | 128/203.15 |
| 6,273,084 B1 | * | 8/2001 | Frid ...................... | 128/200.23 |
| 6,273,085 B1 | * | 8/2001 | Eisele et al. ........... | 128/203.15 |
| 6,328,034 B1 | * | 12/2001 | Eisele et al. ........... | 128/203.15 |
| 6,367,473 B1 | * | 4/2002 | Kafer .................... | 128/203.21 |
| 7,252,087 B2 | * | 8/2007 | Wachtel ................ | 128/203.21 |
| 2003/0070679 A1 | | 4/2003 | Hochrainer et al. | |
| 2004/0094146 A1 | * | 5/2004 | Schiewe et al. ........ | 128/200.11 |
| 2007/0221211 A1 | * | 9/2007 | Sagalovich ............ | 128/200.15 |

FOREIGN PATENT DOCUMENTS

| | | |
|---|---|---|
| SU | 1733008 A1 | 11/1989 |
| WO | 02-098874 A2 | 12/2002 |
| WO | WO 03/084502 A1 * | 10/2003 |

* cited by examiner

*Primary Examiner*—Steven O Douglas
*Assistant Examiner*—Annette F Dixon
(74) *Attorney, Agent, or Firm*—Michael P. Morris; Mary-Ellen M. Devlin; David L. Kershner

(57) ABSTRACT

An inhaler for inhaling powdered pharmaceutical compositions from capsules includes: a lower part; a plate which can be latched to the lower part and with which the lower part can be closed off; a capsule holder for receiving the capsules, this holder being adapted to be lowered into the lower part; a mouthpiece latchable to the plate; a lid which covers the mouthpiece in a closed position and latches it by means of a closure element, the lower part, the plate, the mouthpiece and the lid being hinged together by means of a single joint; and an actuating member which can be moved out a resting position and thereby interacts with at least one pin which can be made to pierce the capsule holder.

16 Claims, 3 Drawing Sheets

DRY POWDER INHALER

BACKGROUND

The invention relates to an inhaler for inhaling powdered pharmaceutical compositions from capsules which are inserted in a capsule holder provided in the inhaler before use. After the capsule has been inserted in the capsule holder the patient can press an actuating member which can be moved out of a resting position, thereby cooperating with at least one pin which can stick into the capsule holder. The capsule is pierced by the minimum of one pin and the pharmaceutical composition is released.

An inhaler of this kind is described for example in EP 0703800 B1 or EP 0911047 A1. The inhaler known from the above mentioned specifications has a dish-shaped lower part and an equally dish-shaped lid which fits it, these two parts being capable of being flipped apart for use, about a joint provided in the edge portion. Between the lower part and the lid, a mouthpiece which can also be flipped open and a plate below it with a capsule holder provided underneath also act on the joint. After the individual assemblies have been flipped open the patient can insert a drug-filled capsule in the capsule holder, pivot the plate and capsule holder and the mouthpiece into the lower part and pierce the capsule by means of a spring loaded actuating member projecting laterally from the lower part. The patient being treated then draws the pharmaceutical composition into his airway by sucking on the mouthpiece.

The intention is to improve the known inhalers still further in terms of their handling.

SUMMARY OF THE INVENTION

This aim is achieved according to the invention with an inhaler according to a first embodiment, wherein the actuating member is constructed as a double function actuating member by means of which, in a first actuation, the closure element for pivoting the lid can be detached from the lower part, and by means of which, in a second actuation, the procedure for piercing the capsule as described above can be carried out.

An advantage of the invention is that the forces needed to release the lid from the mechanical latching are not introduced directly through the lid but instead through the double function actuating member. This ensures quick and reliable opening of the lid with a clockwork-type mechanism, to make the inhaler ready for use.

In order to allow the lid to be released from the lower part by a clockwork-type mechanism, the double function actuating member has on its upper side a recess which is inclined so as to form a sliding surface for the closure element in the form of a tilting plane and to release the lid from the lower part as the double function actuating member is actuated and hence moved forward. The recess may vary in size. The minimum size must be sufficient to enable the lid to be released from the lower part by a clockwork type mechanism. The maximum size depends on the upper surface of the double function actuating member. The actual opening movement of the lid can then be carried out as previously by actuation of the lid by the patient, opening it fully.

The mouthpiece, which can also be flipped aside, is provided according to the invention with a gripping aid which ensures quick and reliable opening of the mouthpiece. The gripping aid is arranged so that the contact with the mouthpiece is outside the area of the mouthpiece which the patient has to place in his mouth when sucking. The contact surface for opening and the contact surface for sucking are clearly separated from one another thanks to the shape and appearance of the mouthpiece. Consequently, the mouthpiece has an appearance which is improved both optically and practically, which enables the user to handle it intuitively and at the same time ensures optimum hygiene. This is particularly important in the region of the mouthpiece as this component is placed in the mouth when the inhaler is used.

The clockwork-like opening mechanism for the lid according to the invention and the gripping aid on the mouthpiece according to the invention are of great importance, particularly at the start of an asthma attack, as they provide a secure grip and an effective arrangement for patients who would otherwise find it difficult to use the inhaler, possibly because they were suffering from arthritis or had some other restriction to the mobility of their fingers.

In a preferred embodiment, in addition to the spring element between the double function actuating member and the capsule holder for assisting the return of the double function actuating member, at least one other spring element may be provided between the plate and lower part, to assist the opening movement, this additional spring element allowing the lid and/or the mouthpiece to spring open, if the dimensions are suitably selected, thereby completing the clockwork-like opening mechanism.

Preferably, the double function actuating member is movably mounted on the plate or on the capsule holder. The plate and/or capsule holder thus form or forms an abutment for the double function actuating member which slides along the plate when moved from the resting position into the functional position and is guided thereby, for example by means of a guide rail.

In a favourable embodiment, the double function actuating member is spring-loaded. The restoring force which is present even in the resting position ensures that after the double function actuating member has been used it is returned to the resting position and thus the inhaling process can be started or continued.

Advantageously, the double function actuating member comprises a main body and two parallel guide arms engaging thereon. The guide arms project into the lower part and, together with corresponding inserts, e.g. with guide sleeves provided on the outside of the capsule holder, serve to guide the double function actuating member as it moves from the resting position into the various operating positions and back to the resting position.

The guide arms may have end stops at their end remote from the main body, these end stops abutting on the guide sleeves in the resting position. This creates a spring bias on the double function actuating member.

In a preferred embodiment the main body of the double function actuating member has an upper rifled surface and at least one lateral rifled surface. These rifled surfaces are both design elements and help to provide optimum grip during actuation. They are on the main body of the double function actuating member outside the inhalation area and consequently do not come into contact with the patient's mouth area. Moreover, the rifled surfaces may be smaller in area than the rifling of the overall surface and still provide a guarantee of safe and rapid use of the inhaler.

Expediently, the upper rifle surface in the resting position is formed, in its area nearest the lid, with a recess to accommodate the closure element of the lid. Inside the recess the side wall directed towards the lateral rifled surface is inclined so that when the main body is inserted it forms a sliding surface for the closure element and in this way the closure element together with the lid is raised out of the latched position.

Advantageously, the plate latched to the lower part can be detached from the lower part such that the plate can be swivelled away from the lower part. This swivel function makes the inhaler easier to clean. The latching between the plate and lower part can be achieved by means of projecting retaining lugs.

It is also possible to construct all the embodiments of the inhaler such that the double function actuating member with the minimum of one pin that can be stuck into the capsule holder is attached to the plate so that it can be detached from the lower part and swung away, together with the plate latched to the lower part.

Other aspects, features, and advantages of the present invention will be apparent to one skilled in the art from the description herein taken in conjunction with the accompanying drawings.

BRIEF DESCRIPTION OF THE DRAWINGS

To make the invention easier to understand it will now be described more fully with reference to the drawing that follows (FIG. 1).

DETAILED DESCRIPTION OF THE PRESENT INVENTION

Figure 1:
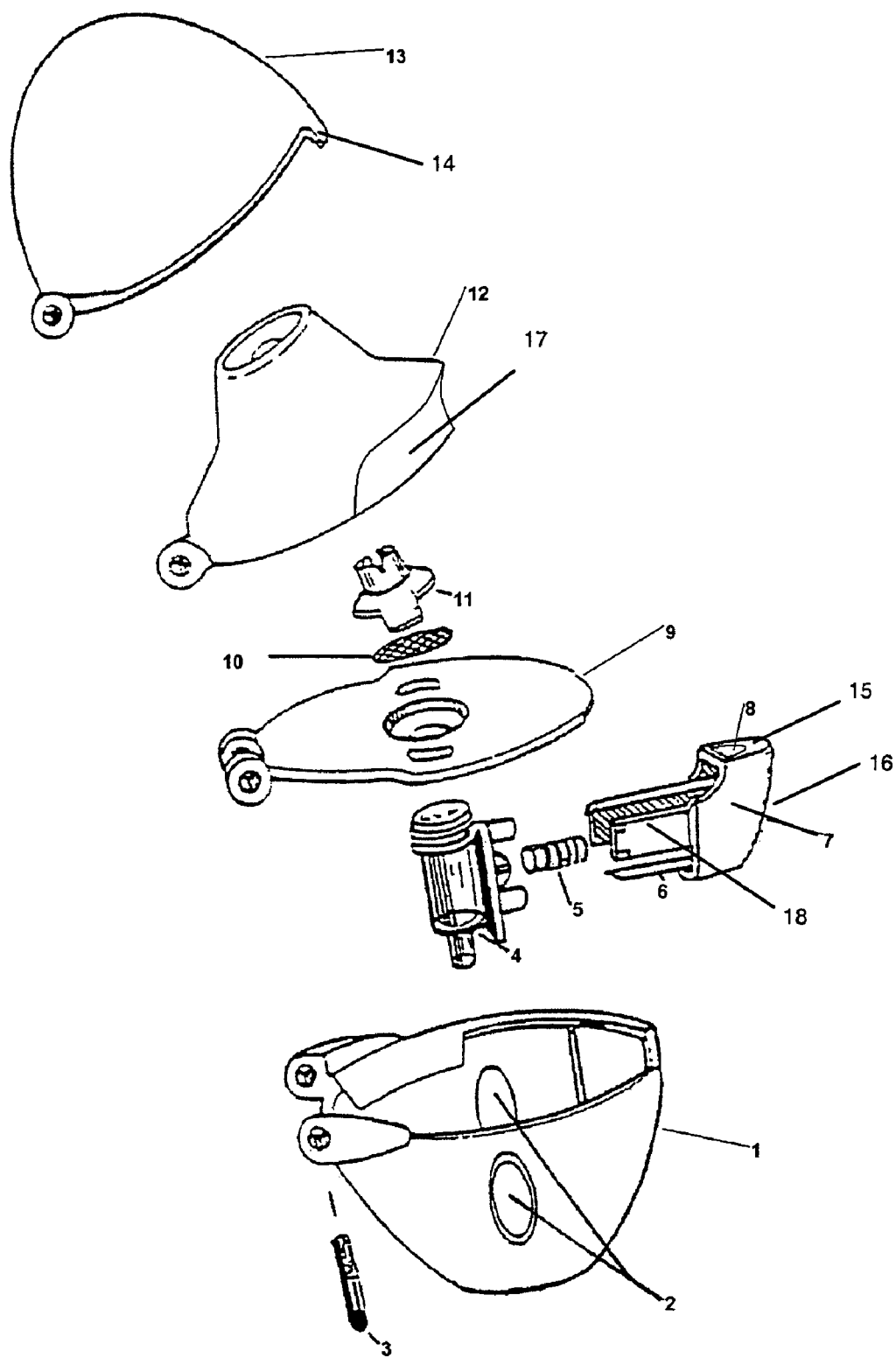
FIG. 1 shows an exploded view with a double function actuating member and mouthpiece with gripping aid.
Figure 2:
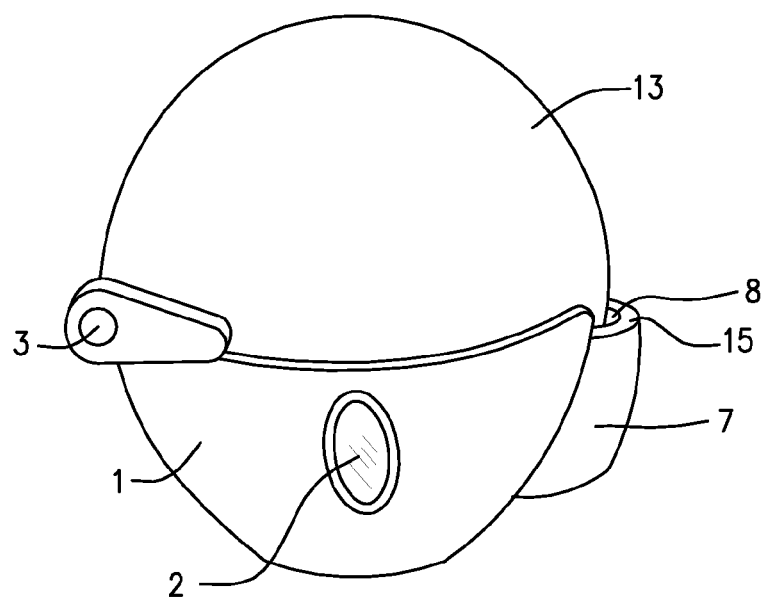
Figure 3:
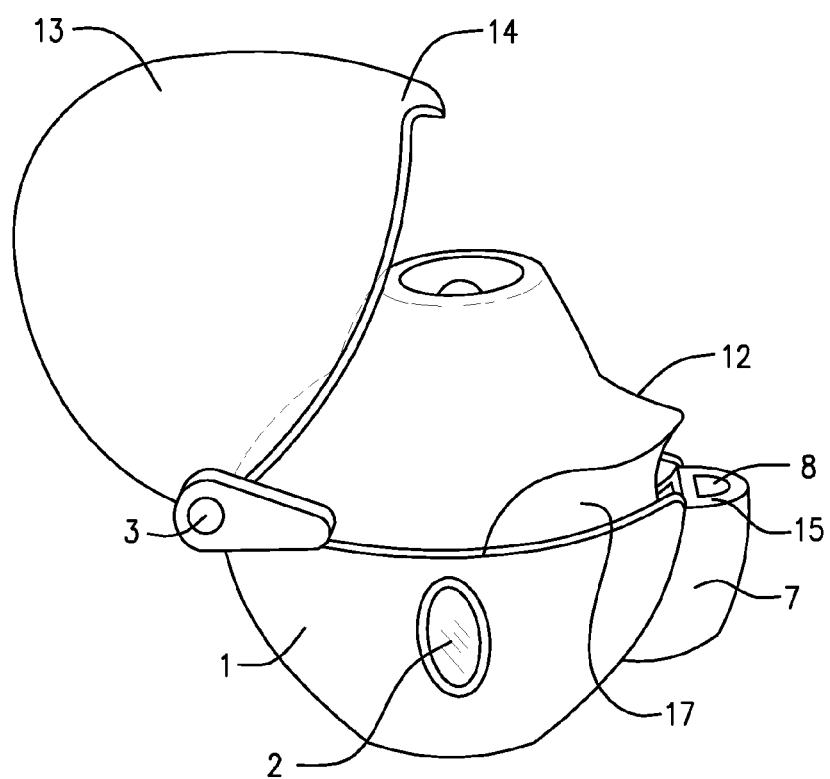

FIG. 1 shows the inhaler in exploded view. The essential components are the lower part 1 which accommodates the plate 9 and is covered by the latter, the mouthpiece 12 with gripping aid 17, said mouthpiece being latchable to the lower part 1 by means of the retaining lugs of the screen holder 11 and the lid 13 which is shaped so as to complement the lower part 1.

In the closed state of the inhaler the closure element 14 on the lid 13 acts on the plate 9 and is held there by frictional engagement. It is also possible to achieve interlocking engagement by the provision of bead-like structures on the closure element 14. For the closure element 14 on the lid 13 to act on the plate 9, the main body of the double function actuating member 7 comprises a recess 8 into which the closure element 14 is lowered as it closes. The recess 8 has an inclined side wall and is located in the area of the upper rifled surface 15 nearest the lid. For particularly reliable operation the double function actuating member 7 is also provided with at least one lateral rifled surface 16.

In order to open the lid 13, first of all the double function actuating member 7 is moved or pressed towards the inhaler. The closure element 14 on the lid 13 makes contact with the inclined side wall of the recess 8 which acts a sliding surface as the main body 7 continues to move forward, and releases the lid 13.

The lower part 1 is cup-shaped and accommodates the entire capsule holder 4 which is mounted on the underside of the plate 9. In order to be able to place a drug filled capsule (not shown) in the capsule holder 4, the mouthpiece 12 also has to be flipped open. In the embodiment shown in FIG. 1 this is done by acting on the gripping aid 17 shown. The gripping aid 17 is preferably implemented by way of a recess, representing a discontinuity in the otherwise smoothly flowing contour of the outside surface of the mouthpiece 12. The recess of the gripping aid 17 may be disposed at a peripheral edge of the mouthpiece 12 near to where the mouthpiece 12 and the plate 9 come into engagement. The specific contour of the recess of the gripping aid may take on many forms, however, it is preferred that the recess easily and comfortably accommodate a user's fingertip(s) so that adequate leverage may be obtained in order to pivot the mouthpiece 12 away from the plate 9 and lower part 1. The recess of the gripping aid 17 preferably initiates at least one lateral side (preferably both lateral sides) of the mouthpiece 12 and extends toward the actuator 7. The discontinuity (or separation) from the smooth contour of the mouthpiece forms a projection at an upper edge of the recess as the contour tapers toward the peripheral edge of the mouthpiece. One of more of the above features enables a user to pivot the mouthpiece 12 away from the plate 9 and lower part 1 without requiring the user to grip the part of the mouthpiece 12 that touches the user's lips, thereby improving the cleanliness of the mouthpiece 12.

In this opened position of the lid 13 and mouthpiece 12 the capsule can be placed in the capsule holder 4 through an opening in the plate 9. Then the mouthpiece 12 is swivelled back again and closed again by the latching of the retaining lugs of the screen holder 11 in the plate 9. In order to release the active substance, at least one pin, but preferably two perpendicularly offset, parallel pins 6 are mounted on the main body of the double function actuating member 7, moving continuously towards the capsule (not shown) as the double function actuating member 7 is pushed in, so as to perforate said capsule. The perforating process can be observed through an inspection window 2.

In the capsule holder 4 there is one or at least two tubular pin guides which is or are directed axially in accordance with the direction of movement of the pin or pins 6. This ensures accurate targeting of the pin or pins on the capsule (not shown) and also provides additional guiding for the double function actuating member 7. However, the essential guiding is achieved by means of two laterally mounted guide arms 18. The guide arms 18 also have the task of holding the double function actuating member 7 under pre-tension. For this, the guide arms 18 are provided, at their ends remote from the main body, with end stops which abut on the guide sleeves of the capsule holder 4 in the resting position of the double function actuating member 7. The guide sleeves are provided on the outside of the capsule holder 4. Between the guide arms 18 is a helical spring 5 which in the axial direction extends parallel to the pin or pins 6, the helical spring 5 being matched to the length of the guide arms 18 such that the double function actuating member 7 is still biased in the resting position.

The individual assemblies of lower part 1, plate 9, mouthpiece 12 and lid 13 are joined together by means of joint sockets and a joint bolt 3 and are all movable or pivotable about this bolt, relative to one another.

The pharmaceutical compositions used for inhalation may be all of kinds of powdered pharmaceuticals which it is therapeutically advisable to administer by inhalation.

Particularly preferred in this context are pharmaceutical compositions selected from among the anticholinergics, beta-2-agonists, steroids, PDE IV-inhibitors, LTD4-antagonists and EGFR-kinase inhibitors.

Anticholinergics for use are preferably selected from among tiotropium bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3', 4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, 2,2-diphenylpropionate cyclopropyltropine methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl 4,4'-difluorobenzilate cyclopropyltropine methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of the racemates, enantiomers or diastereomers thereof and optionally in the form of the solvates and/or hydrates thereof.

Beta-2-agonists used are preferably selected from among albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of the racemates, enantiomers or diastereomers thereof and optionally in the form of ihrer pharmacologically acceptable acid addition salts, solvates and/or hydrates thereof.

The steroids used are preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl6☐,9☐-difluoro-17☐-[(2-furanylcarbonyl)oxy]-11☐-hydroxy-16☐-methyl-3-oxo-androsta-1,4-diene-17☐-carbothionate, (S)-(2-oxo-tetrahydro-furan-3S-yl) 6☐,9☐-difluoro-11☐-hydroxy-16☐-methyl-3-oxo-17☐-propionyloxy-androsta-1,4-diene-17☐-carbothionate and etiprednol-dichloroacetate (BNP-166), optionally in the form of the racemates, enantiomers or diastereomers thereof and optionally in the form of the salts and derivatives thereof, the solvates and/or hydrates thereof.

PDE IV inhibitors used are preferably selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzamide, NCS-613, pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl [4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, CI-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers thereof and optionally in the form of the pharmacologically acceptable acid addition salts thereof, solvates and/or hydrates thereof.

LTD4-antagonists used are preferably selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropanacetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts thereof as well as optionally in the form of the salts and derivatives thereof, the solvates and/or hydrates thereof.

EGFR-kinase inhibitors used are preferably selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]-amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2- buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N—[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

Examples of acid addition salts with pharmacologically acceptable acids which the compounds may be capable of forming include salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Inhalation is an option for powdered pharmaceutical compositions containing the above-mentioned active substances as well as the salts thereof, esters and combinations of these active substances, salts and esters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

LIST OF REFERENCE NUMERALS

1 lower part
2 inspection window
3 articulation bolt
4 capsule holder
5 helical spring
6 pin
7 double function actuating member (main body)
8 recess with sloping side wall as sliding surface
9 plate
10 screen
11 screen holder with retaining lugs
12 mouthpiece with gripping aid
13 lid
14 closure element
15 upper rifled surface of 7
16 lateral rifled surface of 7
17 gripping aid
18 guide arms

The invention claimed is:
1. An inhaler for inhaling powdered pharmaceutical compositions from capsules, comprising:

a lower part, a plate which can be latched to the lower part and with which the lower part can be closed off, and a capsule holder for receiving the capsules, this holder being adapted to be lowered into the lower part, a mouthpiece latchable to the plate, a lid which covers the mouthpiece in a closed position and latches it by means of a closure element, the lower part, the plate, the mouthpiece and the lid being hinged together by means of a single joint, and an actuating member which can be moved out a resting position and thereby interacts with at least one pin which can be made to pierce the capsule holder, wherein:

the mouthpiece has a gripping aid by means of which the mouthpiece can be flipped open, away to the side, the gripping aid disposed proximate to an edge of the mouthpiece and proximate to the actuating member when the mouthpiece is closed the actuating member is constructed as a double function actuating member by means of which, in a first actuation, the closure element can be released from the lower part in order to swivel the lid, and with which, in a second actuation, the capsule is pierced, the actuating member including a recess to receive and engage the closure element when the lid covers the mouthpiece in the closed position.

2. The inhaler according to claim 1, wherein the double function actuating member is movably mounted on the plate and/or capsule holder.

3. The inhaler according to claim 1 or 2, wherein in order to assist the opening movement by the double function actuating member a spring element is disposed between the plate and lower part.

4. The inhaler according to claim 1 or 2, wherein the double function actuating member is movably mounted on the plate.

5. The inhaler according to claim 1 or 2, wherein the double function actuating member is spring loaded.

6. The inhaler according to one of claims 1 or 2, wherein the double function actuating member consists of a main body with two parallel guide arms acting thereon.

7. The inhaler according to claim 6, wherein the main body of the double function actuating member comprises an upper rifled surface and at least one lateral rifled surface.

8. The inhaler according to claim 1 or 2, wherein the double function actuating member has on its upper surface a recess which is inclined so as to form a sliding surface for the closure element in the form of a tilting plane.

9. The inhaler according to claim 1 or 2, wherein the piercing of the capsule is effected by one or more, preferably two, laterally offset, parallel extending pins which are moved by the actuation of the double function actuating member and perforate the capsule.

10. The inhaler according to claim 9, wherein the pin or pins are guided through tubular pin guides.

11. The inhaler according to claim 9 or 10, wherein the pin or pins are each guided through a laterally mounted guide arm.

12. The inhaler according to claim 11, wherein the guide arms mounted laterally hold the double function actuating member under pre-tension.

13. An inhaler for inhaling powdered pharmaceutical compositions from capsules, comprising;

a lower part, a plate which can be latched to the lower part and with which the lower part can be closed off, and a capsule holder for receiving the capsules, this holder being adapted to be lowered into the lower part, a mouthpiece latchable to the plate, a lid which covers the mouthpiece in a closed position and latches it by means of a closure elemental the lower part, the plate, the mouthpiece and the lid being hinged together by means of a single joint, and an actuating member which can be moved out a resting position and thereby interacts with at least one pin which can be made to pierce the capsule holder, wherein the mouthpiece has a gripping aid by means of which the mouthpiece can be flipped open, away to the side, the gripping aid disposed proximate to an edge of the mouthpiece and proximate to the actuating member when the mouthpiece is closed, the actuating member including a recess to receive and engage the closure element when the lid covers the mouthpiece in the closed position.

14. The inhaler according to claim 13, wherein the gripping aid includes a discontinuity from a smooth contour of the mouthpiece at an upper edge thereof, which forms a projection.

15. The inhaler according to claim 13, wherein the gripping aid is of a size suitable for adult patients.

16. The inhaler according to claim 1 or 13 for inhaling powdered pharmaceutical compositions.

* * * * *